United States Patent
Pereira Da Silva et al.

(10) Patent No.: US 12,203,919 B2
(45) Date of Patent: Jan. 21, 2025

(54) METHODS FOR DETECTING AND MAPPING THE SPATIAL DISTRIBUTION OF ORGANIC COMPOUNDS IN RESERVOIR ROCKS AND THE USE THEREOF

(71) Applicants: PETROLEO BRASILEIRO S.A.—PETROBRAS, Rio de Janeiro (BR); UNIVERSIDADE FEDERAL DE GOIAS—UFG, Goiania (BR)

(72) Inventors: Igor Pereira Da Silva, Goiania (BR); Boniek Gontijo Vaz, Goiania (BR); Gesiane Da Silva Lima, Goiania (BR); Iris Medeiros, Jr., Rio de Janeiro (BR); Ruver Rodrigues Feitosa Ramalho, Goiania (BR)

(73) Assignees: PETROLEO BRASILEIRO S.A.—PETROBRAS, Rio de Janeiro (BR); UNIVERSIDADE FEDERAL DE GOIAS—UFG, Goiania (BR)

( * ) Notice: Subject to any disclaimer, the term of this patent is extended or adjusted under 35 U.S.C. 154(b) by 445 days.

(21) Appl. No.: 17/564,849

(22) Filed: Dec. 29, 2021

(65) Prior Publication Data
US 2022/0205969 A1 Jun. 30, 2022

(30) Foreign Application Priority Data
Dec. 30, 2020 (BR) .......................... 1020200269917

(51) Int. Cl.
*G01N 33/24* (2006.01)
*H01J 49/16* (2006.01)

(52) U.S. Cl.
CPC .......... *G01N 33/241* (2013.01); *H01J 49/164* (2013.01); *H01J 49/165* (2013.01)

(58) Field of Classification Search
CPC ..... G01N 33/241; G01N 33/24; H01J 49/164; H01J 49/165
See application file for complete search history.

(56) References Cited

U.S. PATENT DOCUMENTS

| | | | |
|---|---|---|---|
| 2010/0059674 A1* | 3/2010 | Chen | H01J 49/045 250/288 |
| 2011/0084202 A1* | 4/2011 | Finlay | G01N 33/2823 250/254 |
| 2014/0165701 A1* | 6/2014 | Wu | G01N 33/241 73/23.38 |

OTHER PUBLICATIONS

Zou et al., Ambient Mass Spectrometry Imaging with Picosecond Infrared Laser Ablation Electrospray Ionization (PIR-LAESI), 87 Anal. Chem. 12071 (2015) (Year: 2015).*

(Continued)

*Primary Examiner* — David E Smith
(74) *Attorney, Agent, or Firm* — RAPHAEL BELLUM PLLC

(57) ABSTRACT

The present invention relates to a method for detecting and mapping the spatial distribution of organic compounds aiming to understand how such organic compounds are distributed on the surfaces of reservoir rocks subjected to injection fluids for oil recovery purposes. The DESI and LAESI techniques may be used in the analysis of rocks from trials of oil recovery in small or large scale. Furthermore, both techniques may be applied in the analysis of compounds present on the surfaces of minerals from aquatic environments.

12 Claims, 9 Drawing Sheets

(56) References Cited

OTHER PUBLICATIONS

Soparawalla et al., "Trace Detection of Non-Uniformly Distributed Analytes On Surfaces Using Mass Transfer and Large-Area Desorption Electrospray Ionization Mass Spectrometry", Analyst, 2010, 135, 1953-1960 (Year: 2010).*
Benassi, M.; Berisha, A.; Romao, W. et al., "Petroleum crude oil analysis using low-temperature plasma mass spectrometry", Rapid Communications in Mass Spectrometry, v. 27, p. 825-834, 2013.
Soparawalla, S.; Salazar, G. A.; Sokol, E. et al., "Trace detection of non-uniformly distributed analytes on surfaces using mass transfer and large-area desorption electrospray ionization (DESI) mass spectrometry", The Analyst, v. 135, p. 1953, 2010.
Kauppila, T. J.; Kostiainen, R., "Ambient mass spectrometry in the analysis of compounds of low polarity", Analytical Methods, v. 9, p. 4936-4953, 2017.

* cited by examiner

METHODS FOR DETECTING AND MAPPING THE SPATIAL DISTRIBUTION OF ORGANIC COMPOUNDS IN RESERVOIR ROCKS AND THE USE THEREOF

FIELD OF THE INVENTION

This invention addresses methods for detecting and mapping the spatial distribution of organic compounds for use in the reservoir modeling, simulation, and assessment field, in order to understand how the organic compounds are distributed on the surfaces of reservoir rocks subjected to injection fluids for oil recovery purposes.

DESCRIPTION OF THE STATE-OF-THE-ART

Rocks are major oil reservoirs and are consequently subjected extensively to oil extraction processes. Oil is extracted from reservoir rock through a process known as recovery, which must be extremely efficient in order to ensure adequate economic returns. In small-scale recovery tests run to ascertain the best oil removal method/fluid, there is a need to check which compounds remain in the region whether recovery fluid was injected, as well as the compounds found in the extraction region. Consequently, it is necessary to use analytical techniques with high sensitivity and selectivity for detecting, identifying, and mapping the spatial distribution of organic compounds on rock surfaces.

Mass spectrometry is an analytical technique that can be used to detect and identify a wide variety of compounds. Moreover, mass spectrometry may also be used to investigate the spatial distribution of certain compounds on surfaces of interest through the chemical imaging analysis method. Both used in mass spectrometry analyses, the Desorption Electrospray Ionization (DESI) and Laser Ablation Electrospray Ionization (LAESI) ionization techniques are appropriate for detecting, identifying, and performing chemical imaging for a variety of compounds on solid sample surfaces, was no need for pre-treatment thereof. Consequently, both these techniques appear as potential technologies for analyzing organic compounds on reservoir rock surfaces through oil recovery tests.

The Desorption Electrospray Ionization (DESI) and Laser Ablation Electrospray Ionization (LAESI) techniques are widely used for detecting, identifying chemical imaging molecular species on the surfaces of assorted samples. The DESI technique uses a charged droplet spray (electrospray) that is pneumatically directed towards the sample surface for desorbing and ionizing analytes of interest. After desorption/ionization, the ions are directed towards the mass spectrometer entrance for subsequent detection. The analysis is thus performed directly on the sample surface, with no need for extensive pre-treatment thereof prior to the mass spectrometry analysis. If the spray is used to sweep across the sample surface, a mass spectrum may be recorded at all points where the sweep occurs, allowing a definition of the spatial distribution of assorted molecular species. Consequently, chemical images may be generated, plotting the intensities of the signal of the analyte of interest within a 2-D space corresponding to the sample area covered by the spray.

The LAESI technique uses the infrared wavelength laser to desorb the analytes of interest. Laser beams at a 2.9 μm wavelength are commonly used to desorb samples containing water, as this wavelength excites O—H bonds in water molecules, causing an alteration in the analyte phase and desorption of neutral particles. However, if the laser wavelength is adjusted to 3.4 μm, the C—H bonds may be excited, allowing the desorption of molecules with lower polarity. After desorption, the molecules interact with a charged droplet spray located above the sample. The analytes are thus ionized and directed towards the mass spectrometer entrance. Similar to the DESI technique, the sample surface may be swept, allowing chemical imaging and the spatial location of analytes of interest.

Due to the characteristics described above, the DESI and LAESI techniques have been widely used to map the chemical distribution of many compounds (such as drugs of abuse, pesticides, lipids etc.) on the surfaces of animal and plant tissues. These applications give rise to other hypotheses, such as the possibility of using these techniques to detect and map organic compounds on reservoir rock surfaces.

The document authored by BENASSI, M.; BERISHA, A.; ROMÃO, W. et al. Entitled "Petroleum crude oil analysis using low-temperature plasma mass spectrometry", Rapid Communications in Mass Spectrometry, v. 27, p. 825-834, 2013 discloses a crude oil analysis with no sample preparation or dilution, conducted directly on the sampling surfaces of different materials, such as polytetrafluoroethylene, glass and polyethylene. Desorption ionization techniques, such as Direct Analysis In Real Time (DART) and DESI, play vital roles in the establishment of ambient mass spectrometry, as both are able to desorb and ionize analytes directly on a sampling surface or on the actual sample.

Studies conducted by SOPARAWALLA, S.; SALAZAR, G. A.; SOKOL, E. et al. on "Trace detection of non-uniformly distributed analytes on surfaces using mass transfer and large-area desorption electrospray ionization (DESI) mass spectrometry", The Analyst, v. 135, p. 1953, 2010 referred to a Rhodamine 6G analysis and several drugs of abuse (codeine, heroin and diazepam) on a DESI source. Ambient ionization methods use different desorbing and ionizing agents, which include Desorption Atmospheric Pressure Chemical Ionization (DAPCI), Laser Ablation Electrospray Ionization (LAESI), Electrospray Laser Desorption/Ionization (ELDI), Plasma-Assisted Laser Desorption/Ionization (PADI), Low Temperature Plasma (LTP) Desorption/Ionization, Direct Analysis In Real Time (DART), Desorption Sonic Spray Ionization (DeSSI) and Dielectric Barrier Discharge (DBDI).

The reference authored by KAUPPILA, T. J.; KOSTIAINEN, R. on "Ambient mass spectrometry in the analysis of compounds of low polarity", Analytical Methods, v. 9, p. 4936-4953, 2017 discloses several types of ambient mass spectrometry techniques that can ionize low-polarity compounds, such as DART, LAESI, Atmospheric Solids Analysis Probe (ASAP), Dielectric Barrier Discharge Ionization (DBDI), and Desorption Atmospheric Pressure Photoionization (DAPPI).

However, the document constituting the state-of-the-art discloses a combination of the DESI and LAESI techniques for detecting and mapping the spatial distribution of organic compounds on reservoir rock surfaces, as presented in this invention.

Consequently, this invention was developed in order to solve these problems, through the use of the DESI and LAESI techniques, in order to understand how compounds are distributed on the surfaces of rocks subjected to injection fluids for oil recovery purposes. Using both techniques, it is possible to check the region where a specific compound is more concentrated, providing insights for strategic formulations used for applying the recovery fluid.

Furthermore, the DESI and LAESI techniques may be useful for identifying unknown compounds on the surfaces of reservoir rocks collected in aquatic environments for studying how certain compounds are distributed naturally on sedimentary rock surfaces.

This invention is thus a unique way of analyzing organic composition directly on reservoir rocks through mass spectrometry, using a combination of the DESI and LAESI sources.

BRIEF DESCRIPTION OF THE INVENTION

This invention addresses methods for detecting and mapping the spatial distribution of organic compounds comprising the joint use of the DESI and LAESI techniques in order to understand how compounds are distributed on the surfaces of rocks subjected to injection fluids for oil recovery purposes.

The DESI and LAESI techniques may be used for analyzing rocks through small or large scale oil recovery experiments. Furthermore, both techniques may be used to analyze compounds found on the surfaces of minerals deriving from aquatic environments. The DESI technique has the potential for use in analyzing polar compounds, while the LAESI technique may be used for analyzing high and low polarity molecular species.

BRIEF DESCRIPTION OF THE DRAWINGS

This invention is described in greater detail below, referring to the Figures appended hereto that provide examples of the impediment thereof in a schematic manner that does not impose any constraints on the scope of this invention. The drawings show.

DETAILED DESCRIPTION OF THE INVENTION

The method for detecting and mapping the spatial distribution of organic compounds comprises a combination of two mass spectrometry ionization techniques called Desorption Electrospray Ionization (DESI) and Laser Ablation Electrospray Ionization (LAESI) for detecting, identifying, and mapping the spatial distribution of organic compounds on reservoir rock surfaces.

The DESI technique may be used to analyze polar compounds, while the LAESI technique may be used to determine low-polarity compounds. Both techniques are widely used for analyzing organic compounds on plant and animal tissue surfaces, but have never been used for studying molecular species on rock surfaces.

Figure 1:
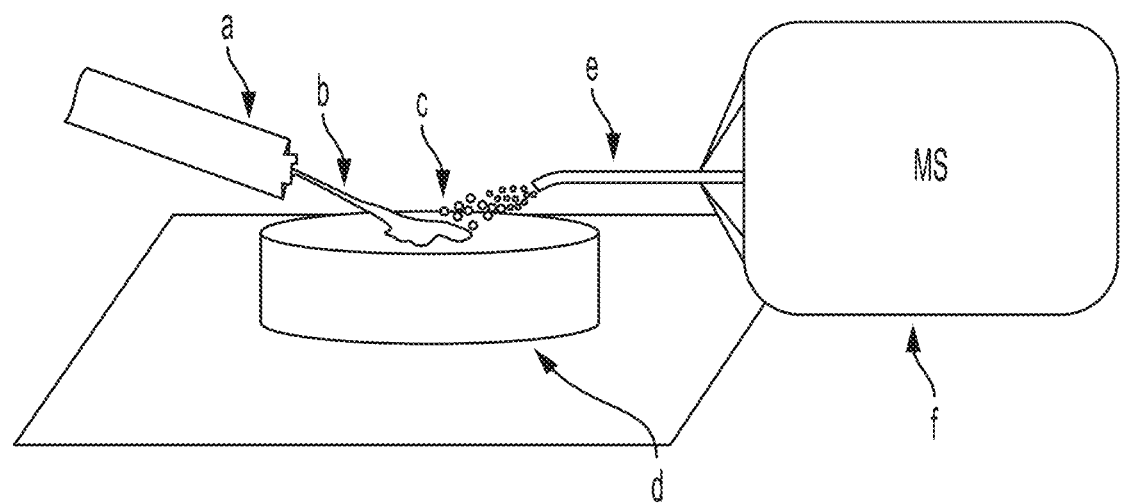
FIG. 1 illustrates an overview of the DESI technique for analyzing organic compounds on a reservoir rock surface: (a) tube emitting a charged particle spray; (b) charged particle spray; (c) ionization and desorption process of analytes on the rock surface; (d) reservoir rock; (e) ion transfer tube; (f) mass spectrometer.
Figure 2A:
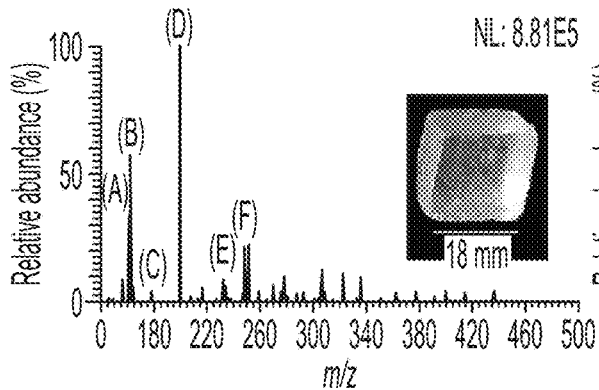
FIG. 2 illustrates analyses of the following rocks (a) Optical Calcite, (b) Quartz, (c) Dolomite, (d) Berea Sandstone and (e) Pink by DESI technique after applying a methanolic solution of 10 ppm of the following acids: (A) cyclohexane butyric, (B) decanoic, (C) 1-naphthalene acetic, (D) 3,5-dimethyl adamantane-1-carboxylic, (E) pentadecanoic and (F) palmitic. All mass spectra were obtained in negative ionization mode.
Figure 2B:
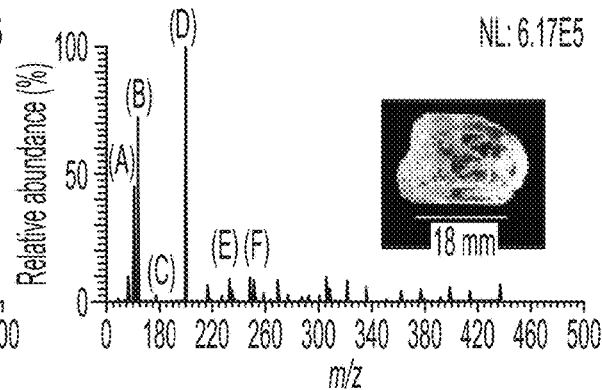
Figure 2C:
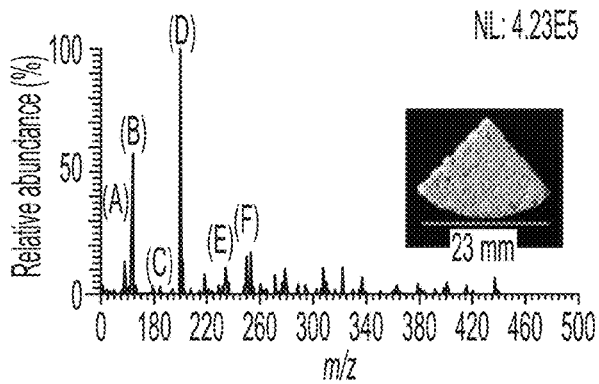
Figure 2D:
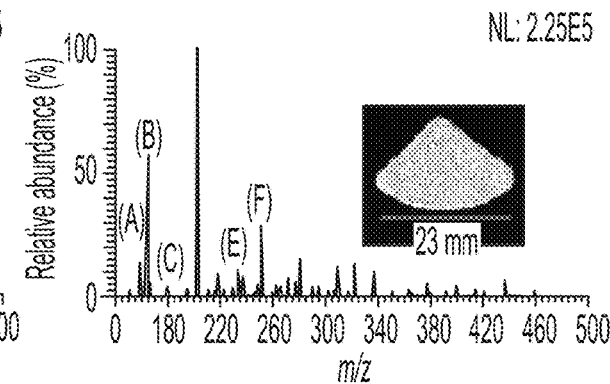
Figure 2E:
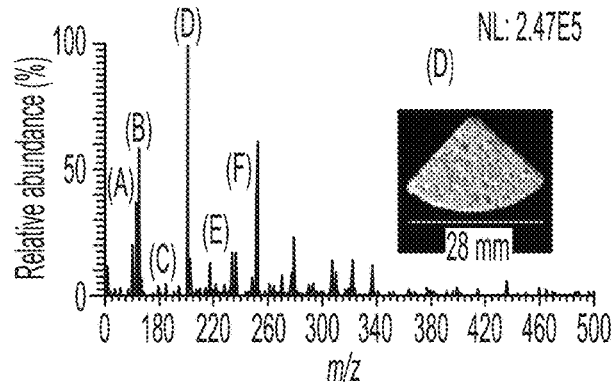
Figure 3A:
FIG. 3 illustrates the assessment of the different solvent analysis systems on the surface 1 of the HCB3-1 rock by the DESI technique: (a) MeOH; (b) MeOH/Tol (7:3); (c) MeOH/Tol (6:4); (d) MeOH/Tol (5:5). All mass spectra were obtained in negative ionization mode.
Figure 3A:
Figure 3B:
Figure 3C:
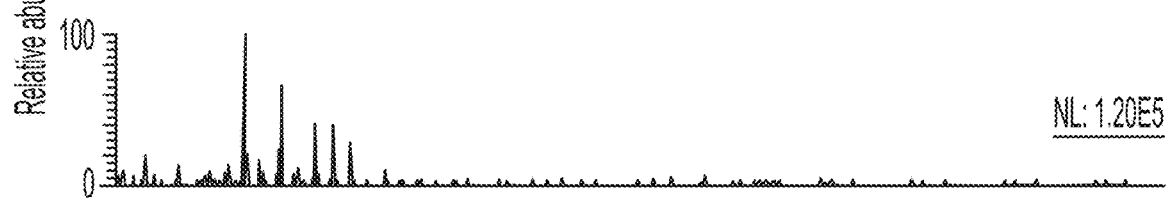
Figure 3D:
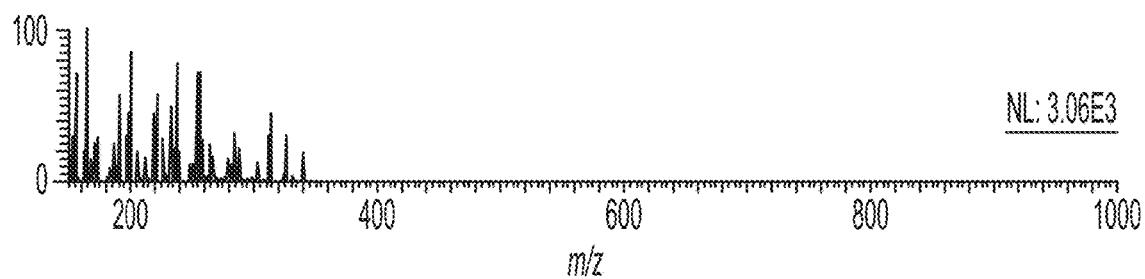
Figure 4A:
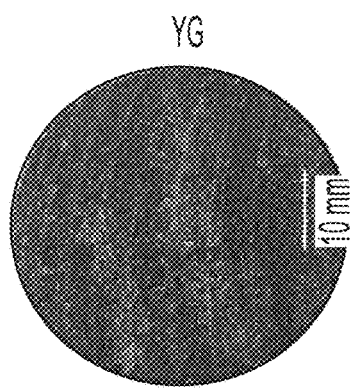
FIG. 4 illustrates the assessment of the different solvent analysis systems on the surface 1 of the YG rock by the DESI technique: (a) MeOH; (b) MeOH/Tol (7:3); (c) MeOH/Tol (6:4); (d) MeOH/Tol (5:5). All mass spectra were obtained in positive ionization mode.
Figure 4A:
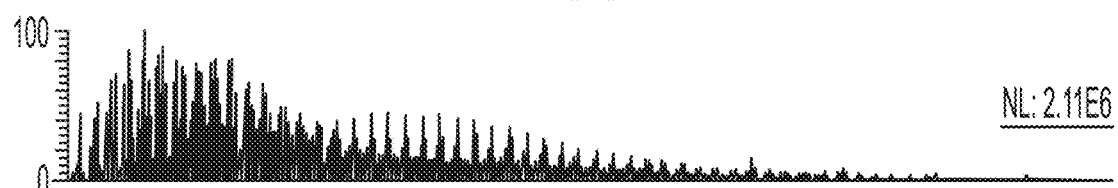
Figure 4B:
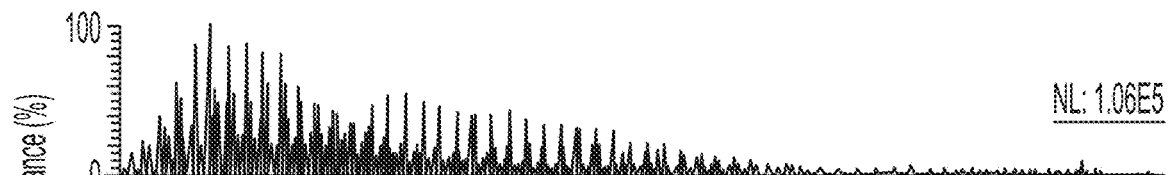
Figure 4C:
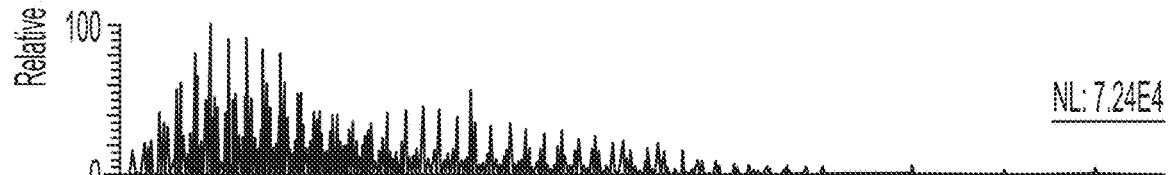
Figure 4D:
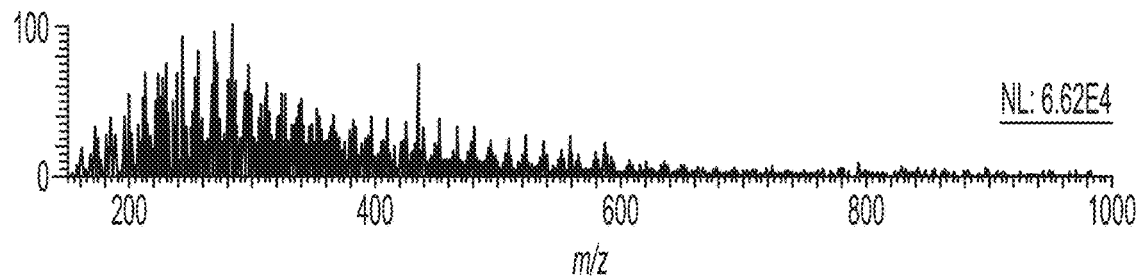
Figure 5A:
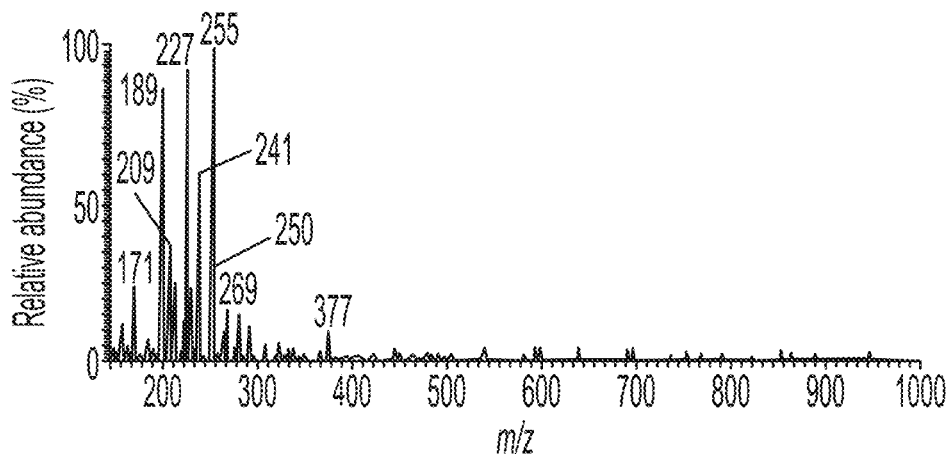
FIG. 5 illustrates chemical imaging by the DESI technique of compounds on different rock surfaces: (a) mass spectrum (negative mode) representative of all the rocks; (b) HCB3-1 (surface 1); (c) HCB3-1 (surface 2); (d) HCB3-2 (surface 1); (e) HCB3-2 (surface 2); (0 IGE (surface 1); (g) IGE (surface 2)
Figure 5B:
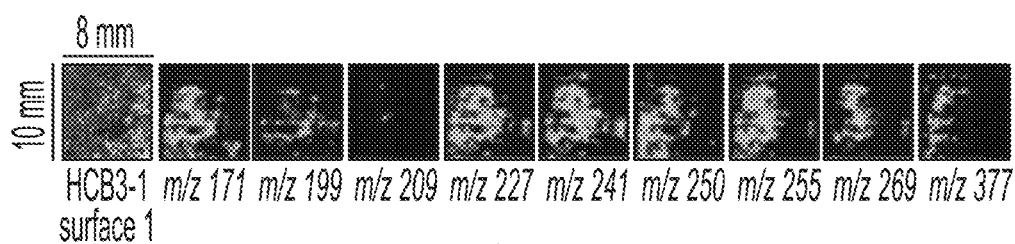
Figure 5C:
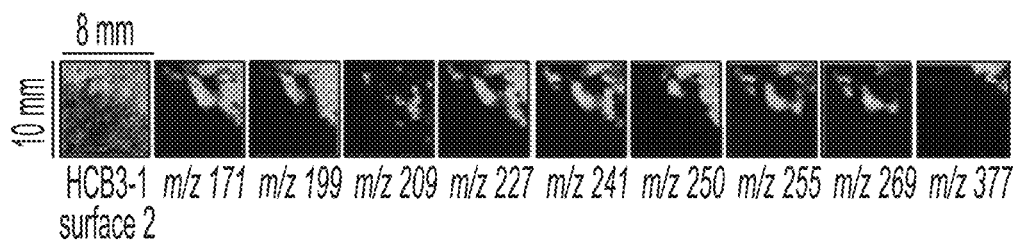
Figure 5D:
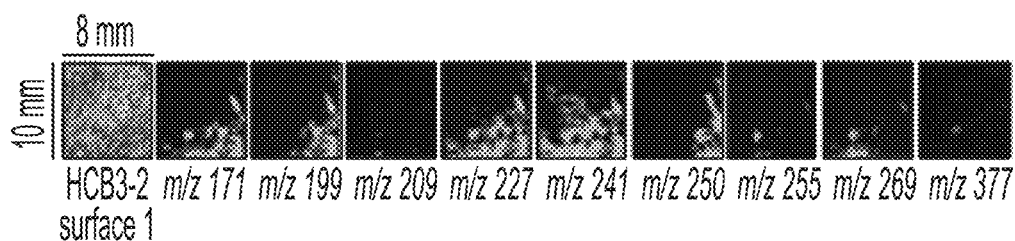
Figure 5E:
Figure 5F:
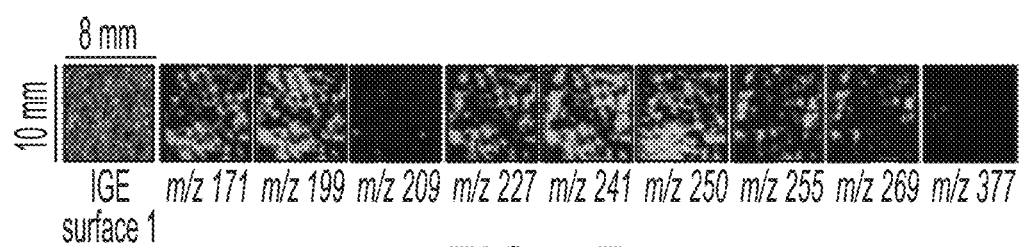
Figure 5G:
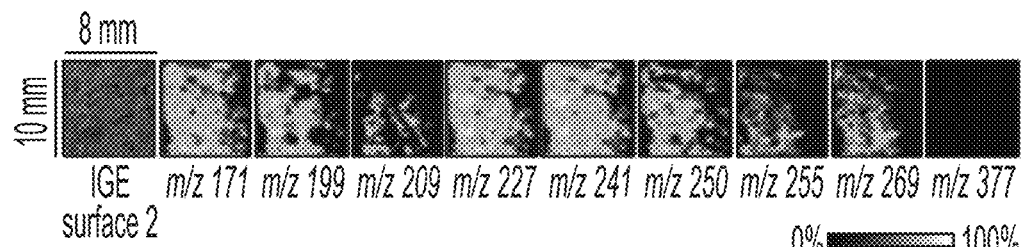

As shown in FIG. 1, the analysis using the DESI technique is performed by using the DESI-2D source connected to a mass spectrometer. The exact identification of the compounds in the samples is handled through high mass accuracy and high resolution. Analytes on the sample surface are extracted and ionized through a charged particle spray. in order to generate the spray, a silica capillary with an internal diameter of 50 µm in its a solvent, such as methanol, or a 1:1 methanol/toluene or methanol/water solvent mixture with a flow of 2 µL/min, while an external silica capillary with an internal diameter of 250 µm emits nitrogen gas with typical pressure of 150 psi. This spray is pneumatically directed towards the surface of the rock, which is deposited on a platform moving along the X and Y axes.

Experiments are performed under identical experimental conditions, including geometrical parameters, such as a distance of approximately 2 mm from the tip of the electrospray capillary to the sample surface, with the spray angled at 55°, at a distance of approximately 5 mm between the spray spot and the entrance to the mass spectrometer. For the chemical imaging experiments, the sample rock surfaces are swept by the spray in a single continuous horizontal movement and with a 200 µm vertical pass (spatial resolution).

The FireFly software (version 2.0) is used to convert the mass spectra files from Xcalibur 2.2 into a format compatible with the BioMap software, in order to construct spatially accurate 2D ion images. The rainbow color palette is used in the BioMap software to display signal intensity.

Figure 7:
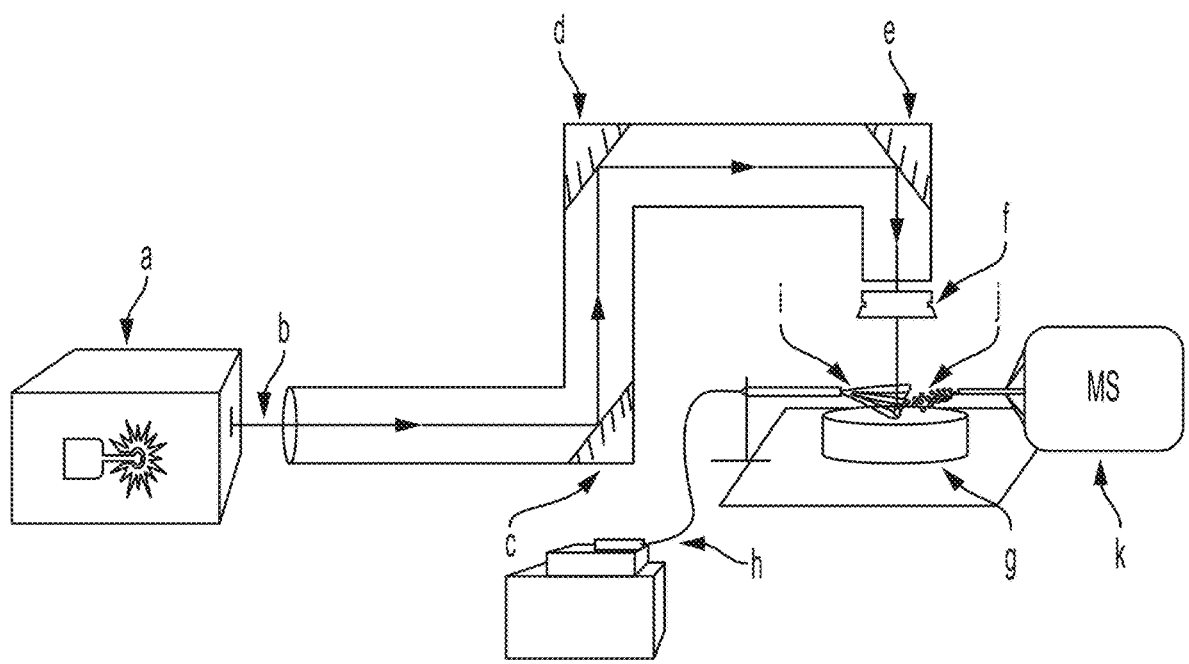
FIG. 7 illustrates an overview of the LAESI technique for analyzing organic compounds on reservoir rock surfaces: (a) infrared resonant optical parametric oscillator with adjustable wavelengths (2900 to 3450 nm); (b) laser beam; (c) mirror 1; (d) mirror 2; (e) mirror 3; (0 laser beam focus lens; (g) reservoir rock; (h) solvent injection pump; (i) charged particle spray; (j) generation of gas-phase analyte ions (k) mass spectrometer.

As shown in FIG. 7, an analysis through the LAESI technique uses an Infrared resonant optical parametric oscillator adjustable wavelengths varying from 2.9 to 3.4 µm and is used to irradiate laser beams onto the sample at a 90° angle. The laser beam wavelength may be adjusted to 2.9 µm in order to excite the O-H bonds (for polar molecule analyses), or adjusted to 3.4 µm to excite the C-H bonds (for low-polarity molecule analyses). Mirrors are used to direct the laser beam towards the sample, and a calcium fluoride plano-convex lens is used to focus the laser at a distance of 50 mm. The laser spot size is 150 to 180 µm, measured after laser beam irradiation on thermal paper. The laser beam is directed to the sample surface at a frequency of 10 Hz and with typical energy of 2.5 mJ. The rock sample is placed on a mobile platform, as described above for analyses using the DESI technique.

The material irradiated by the laser is desorbed and ionized by a charged droplet spray from an electrospray source located above the sample. The following geometrical parameters are optimized and used in the analyses: distance between the electrospray capillary and the ion transfer tube: 16 mm; distance between the electrospray capillary and the sample surface: 10 mm; distance between the focus lens and the sample surface: 50 mm.

A solvent such as methanol for example, or a 1:1 methanol/water solvent mixture with a flow of 1.5-2.0 µL/min is used as the electrospray solvent. The analyses are performed through the use of a mass spectrometer. For the chemical imaging experiments, the sample rock surfaces are irradiated by the laser beam in a continuous horizontal movement and with one 200 µm vertical pass (spatial resolution).

The FireFly software (version 2.0) is used to convert the mass spectra files from Xcalibur 2.2 into a format compatible with the BioMap software, in order to construct spatially accurate 2D ion images. The rainbow color palette is used in the BioMap software to display signal intensity.

EXAMPLES

The following examples illustrate some particular embodiments of this invention, and may not be construed as imposing constraints thereon.

Example 1: DESI Technique

As shown in FIG. 5, the DESI technique was used to perform the chemical imaging of the compounds on the surfaces of the HCB3-1, HCB3-2 and IGE rocks, collected in the Araripe Basin. Two surfaces (both sides) of each rock were analyzed.

Although thousands of compounds were detected and imaged, only nine are shown in FIG. 5. Each ion was normalized to 100% intensity separately. The nine compounds are identified in detail (exact m/z values; exact figures for masses and molecular formulas) in Table 1. Eight of these compounds were identified as carboxylic acids, and are distributed differently on each rock surface. One ion was identified as sugar (saccharose, [M+Cl]⁻), and its distribution was specific for each rock. As the saccharose and other sugars may be produced by plants, the presence of this compound can be explained through contact between the rocks and aquatic plants in the Araripe Basin.

These findings demonstrate that the DESI-MS technique is a useful tool for investigating the spatial distribution of assorted molecular species on rock surfaces, and may provide insights into how certain compounds cluster on rock surfaces in aquatic or land environments.

TABLE 1

The m/z values, errors (ppm), and molecular formulas for the nine compounds as shown in FIG. 1. The ions were through using a high-resolution mass spectrometer (Thermo Scientific Q Exactive Hybrid Quadrupole-Orbitrap)

| m/z | Error (ppm) | Molecular Formula | Attempted Identification |
|---|---|---|---|
| 171.13913 | 0.449 | $[C_{10}H_{20}O_2 - H]^-$ | decanoic acid |
| 199.17047 | 0.586 | $[C_{12}H_{24}O_2 - H]^-$ | dodecanoic acid |
| 209.09334 | 0.834 | $[C_{10}H_{14}O_3N_2 - H]^-$ | 3-(4-acetyl-3,5-dimethyl pyrazolyl) propanoic acid |
| 227.20184 | 0.821 | $[C_{14}H_{28}O_2 - H]^-$ | tetradecanoic acid |
| 241.21751 | 0.856 | $[C_{15}H_{30}O_2 - H]^-$ | pentadecanoic acid |
| 250.14505 | 0.732 | $[C_{14}H_{21}O_3N - H]^-$ | 3-amino-3-(4-pentoxiphenyl) propanoic acid |
| 255.23317 | 0.848 | $[C_{16}H_{32}O_2 - H]^-$ | hexadecenoic acid |
| 269.24872 | 0.432 | $[C_{17}H_{34}O_2 - H]^-$ | heptadecanoic acid |
| 377.08582 | 0.551 | $[C_{12}H_{22}O_{11} + Cl]^-$ | Saccharose |

Example 2: DESI Technique

Figure 6A:
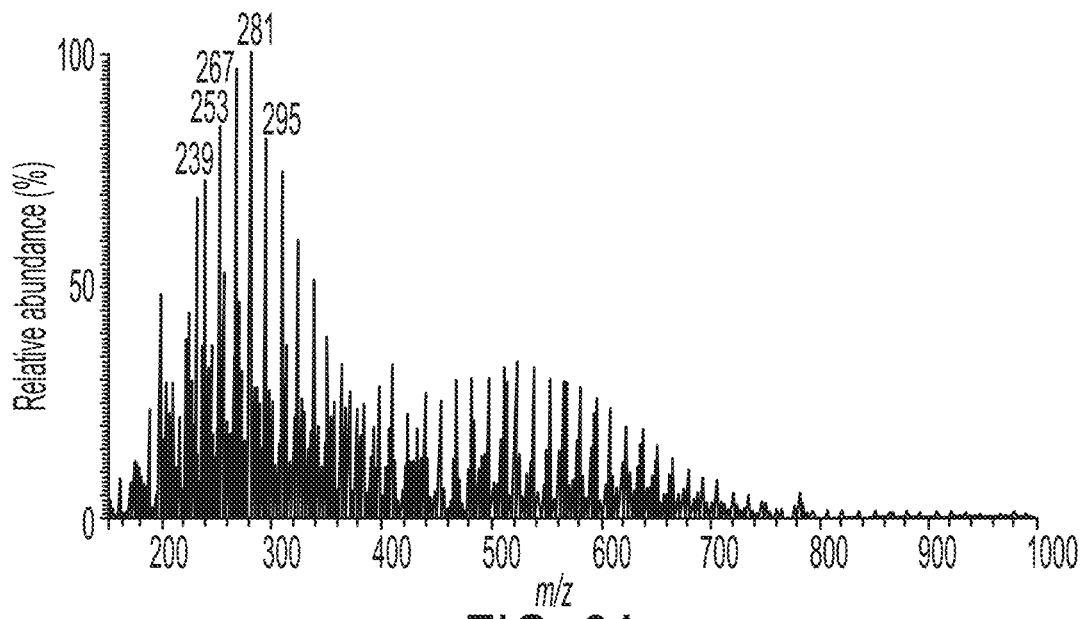
FIG. 6 illustrates the chemical imaging by the DESI technique of compounds on the YG rock: (a) mass spectrum (positive mode) representative of both rock surfaces; (b) surface 1; (c) surface 2.
Figure 6B:
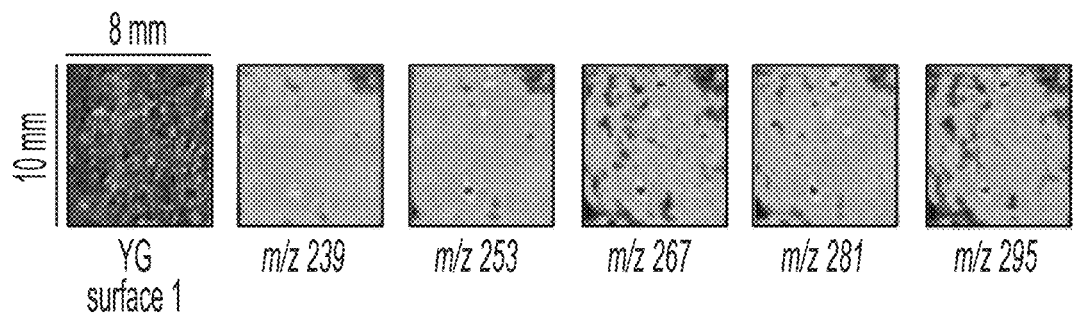
Figure 6C:
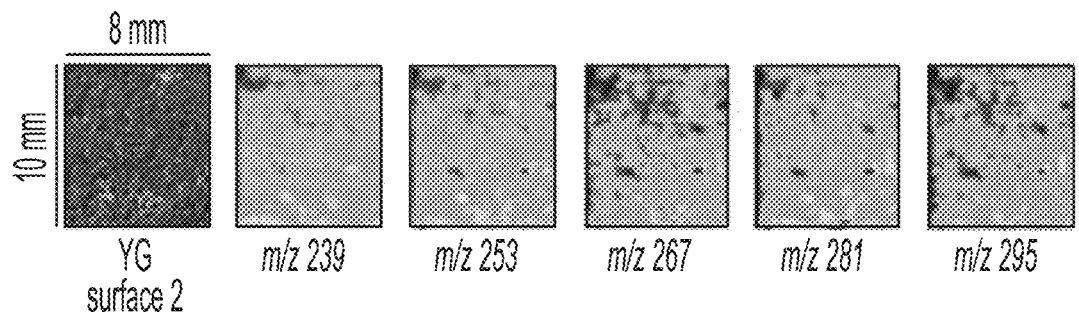

FIG. 6 shows the chemical imaging results for the YG rock obtained by the DESI technique. The YG rock is a Berea sandstone taken from a small-scale recovery experiment using glycerin-based drilling fluids.

Both rock surfaces were analyzed and, although thousands of compounds were detected and imaged, only five are shown in FIG. 6. These compounds are identified in detail in Table 2. Few differences were found in the distributions of the different ions on the same surface, although they were distributed differently on different surfaces.

These findings suggest that chemical imaging by the DESI technique is an analytical approach with potential used for determining the exact location of compounds left over from oil recovery experiments on reservoir rocks.

TABLE 2

The m/z values, errors (ppm), and molecular formulas for the five compounds as shown in FIG. 2.

| m/z | Error (ppm) | Molecular Formula |
|---|---|---|
| 239.14322 | 0.745 | $[C_{18}H_{18}O + H]^+$ |
| 253.15890 | 0.822 | $[C_{18}H_{20}O + H]^+$ |
| 267.17453 | 0.704 | $[C_{19}H_{22}O + H]^+$ |
| 281.19021 | 0.775 | $[C_{20}H_{24}O + H]^+$ |
| 295.20587 | 0.772 | $[C_{21}H_{26}O + H]^+$ |

Example 3: LAESI Technique

The LAESI technique was used to detect and map the chemical distribution of the organic compounds on the YG rock surfaces. The laser beam wavelength was adjusted to 3.4 µm in order to excite the C—H bonds and promote the desorption of low-polarity molecules. The laser was used in the same region analyzed by the DESI-MS technique, in order to compare the chemical profiles obtained through each of these techniques.

Figure 8A:
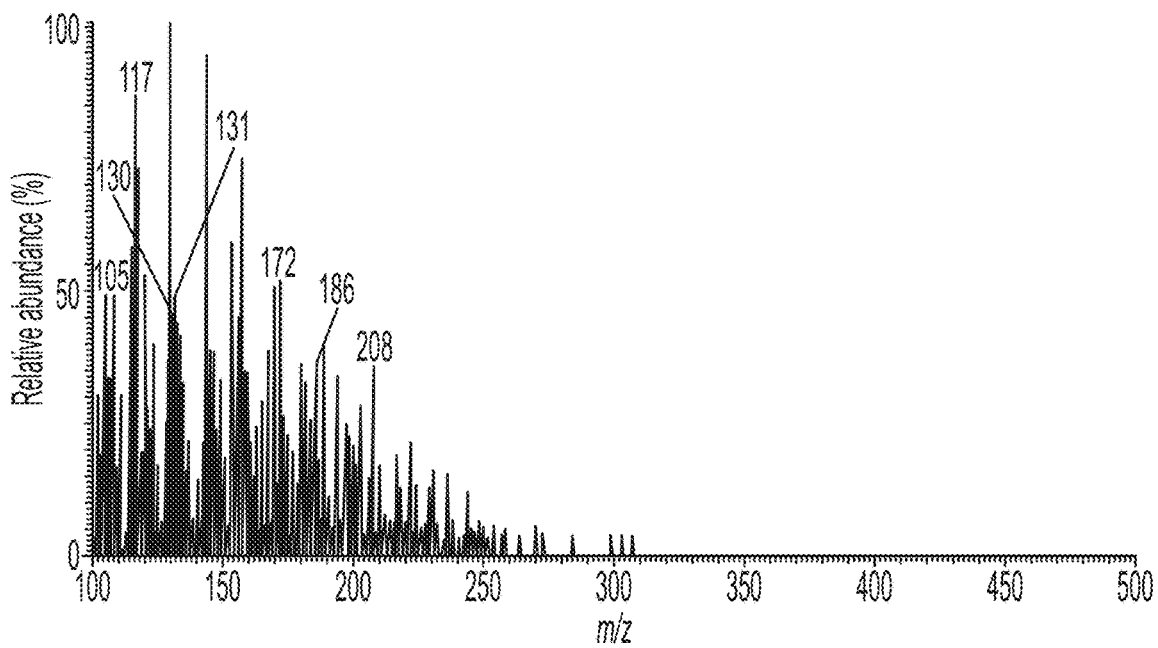
FIG. 8 illustrates chemical imaging through the LAESI technique of compounds on the YG rock: (a) mass spectrum (positive mode) representative of both rock surfaces; (b) surface 1; (c) surface 2.
Figure 8B:
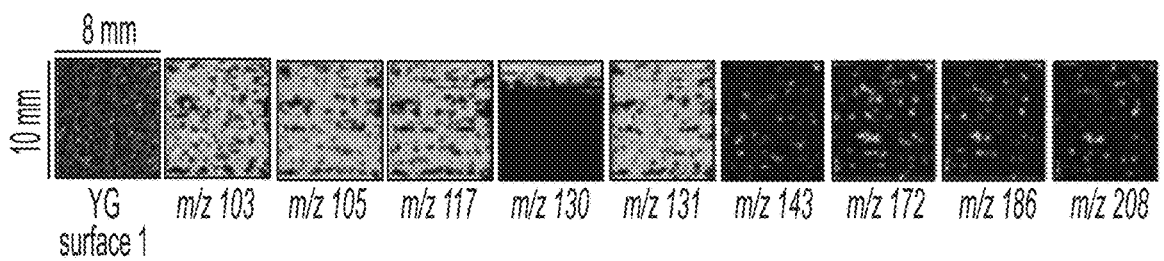
Figure 8C:
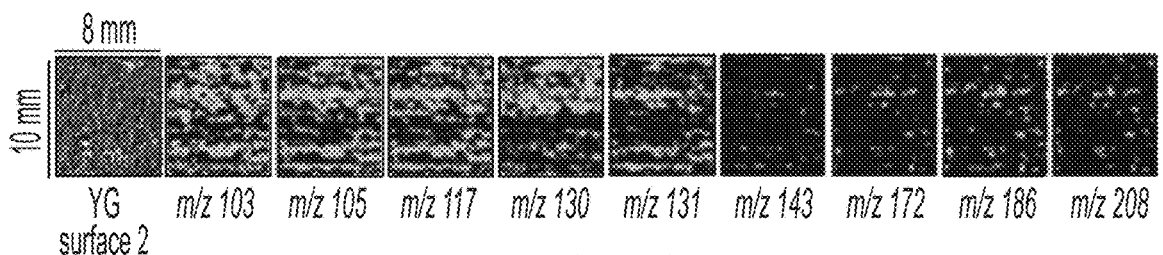

As shown in FIG. 8, the chemical profile obtained through the LAESI technique demonstrated a gaussian with more intense ions in the 100 to 150 m/z region, in contrast to that obtained through the DESI-MS technique (more intense ions in the 250-300 m/z region). Several compounds were detected through the LAESI technique, but only nine of them are shown in FIG. 8. The detailed identification of the ions is presented in Table 3. In addition to ionization through protonation of compounds containing heteroatoms, a notable characteristic of the LAESI technique was the ability to detect radical ions, which allowed the analysis of apolar compounds (hydrocarbons). A possible explanation for this phenomenon is the use of the 3.4 μm infrared laser wavelength.

These findings pave the way for future mapping experiments analyzing apolar compounds in oil samples found on the surfaces of different types of solid materials.

TABLE 3

The m/z values, errors (ppm), and molecular formulas of the nine compounds as shown in FIG. 3

| m/z | Error (ppm) | Molecular Formula |
|---|---|---|
| 103.05430 | 0.710 | $[C_8H_7]^{+-}$ |
| 105.06997 | 0.886 | $[C_8H_9]^{+-}$ |
| 117.06995 | 0.625 | $[C_9H_9]^{+-}$ |
| 130.15910 | 0.567 | $[C_8H_{19}N + H]^+$ |
| 131.08564 | 0.863 | $[C_9H_{11}]^{+-}$ |
| 143.08562 | 0.650 | $[C_{11}H_{11}]^{+-}$ |
| 172.11220 | 0.720 | $[C_{12}H_{13}N + H]^+$ |
| 186.12788 | 0.827 | $[C_{13}H_{15}N + H]^+$ |
| 208.11218 | 0.500 | $[C_{15}H_{13}N + H]^+$ |

It must be noted that, although this invention has been described in terms of the drawings appended hereto, it may be subject to modification and adaptation by persons versed in the art, depending on the specific situation, and provided that this takes place within the scope of the invention defined herein.

The claimed invention is:

1. A method for detecting and mapping the spatial distribution of organic compounds in reservoir rocks, comprising a combination of DESI and LAESI techniques for analyzing reservoir rock surfaces.

2. The method of claim 1, wherein the DESI technique comprises desorbing and ionizing analytes of the surface of the reservoir rock through a spray of charged droplets, wherein the spray is generated by an internal silica capillary that emits a solvent or a mixture of solvents, and an external silica capillary that emits an inert gas; and pneumatically directing the spray towards the sample surface.

3. The method of claim 1, wherein the LAESI technique comprises irradiating the sample surface through a laser beam on the infrared wavelength to desorb the analytes from the surface of the reservoir rock and ionize them through a spray of charged particles located above the sample surface.

4. The method of claim 2, wherein the electrolytic spray solvent is methanol or a 1:1 methanol/toluene mixture.

5. The method of claim 2, wherein the electrolytic spray solvent presents a flow of 2 μL/min.

6. The method of claim 2, wherein the inert gas is nitrogen gas with a pressure of 150 psi.

7. The method of claim 3, wherein the electrolytic spray solvent is methanol or a 1:1 methanol/water mixture.

8. The method of claim 3, wherein the electrolytic spray solvent presents a flow between 1.5 and 2 μL/min.

9. The method of claim 1, wherein the DESI technique is applied to analyze polar compounds.

10. The method of claim 1, wherein the LAESI technique is applied to determine high and low polarity compounds.

11. A method of analyzing rocks from trials of oil recovery in small or large scale, comprising the method of claim 1.

12. A method of analyzing compounds present on the surfaces of minerals from aquatic environments, comprising the method of claim 1.

* * * * *